US012590289B2

(12) United States Patent
Sahin et al.

(10) Patent No.: US 12,590,289 B2
(45) Date of Patent: Mar. 31, 2026

(54) MEDIUM-BASED METHOD REALIZED FOR DIFFERENTIATION OF DENTAL STEM CELLS INTO NEURONS

(71) Applicant: YEDITEPE UNIVERSITESI, Istanbul (TR)

(72) Inventors: Fikrettin Sahin, Istanbul (TR); Pakize Neslihan Tasli, Istanbul (TR); Oguz Kaan Kirbas, Istanbul (TR); Ezgi Avsar Abdik, Istanbul (TR); Huseyin Abdik, Istanbul (TR); Burcu Kasapoglu Usta, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 769 days.

(21) Appl. No.: 17/923,246

(22) PCT Filed: May 4, 2021

(86) PCT No.: PCT/TR2021/050426
§ 371 (c)(1),
(2) Date: Nov. 4, 2022

(87) PCT Pub. No.: WO2021/225552
PCT Pub. Date: Nov. 11, 2021

(65) Prior Publication Data
US 2023/0159888 A1 May 25, 2023

(30) Foreign Application Priority Data
May 4, 2020 (TR) ................................. 2020/06919

(51) Int. Cl.
*C12N 5/0793* (2010.01)
(52) U.S. Cl.
CPC ........ *C12N 5/0619* (2013.01); *C12N 2500/32* (2013.01); *C12N 2500/36* (2013.01); *C12N 2500/38* (2013.01); *C12N 2501/11* (2013.01); *C12N 2501/115* (2013.01); *C12N 2501/13* (2013.01); *C12N 2506/1361* (2013.01)
(58) Field of Classification Search
None
See application file for complete search history.

(56) References Cited

U.S. PATENT DOCUMENTS

2016/0296669 A1 10/2016 Tezuka et al.

FOREIGN PATENT DOCUMENTS

| CN | 1590537 A | 3/2005 |
|----|-----------|--------|
| CN | 104726406 A | 6/2015 |
| CN | 104726406 B | 5/2018 |

OTHER PUBLICATIONS

Heng, Boon Chin, et al. "Small molecules enhance neurogenic differentiation of dental-derived adult stem cells." Archives of oral biology 102 (2019): 26-38. (Year: 2019).*
Lepski, Guilherme, et al. "CAMP promotes the differentiation of neural progenitor cells in vitro via modulation of voltage-gated calcium channels." Frontiers in cellular neuroscience 7 (2013): 155. (Year: 2013).*
Gibco Product Sheet. GlutaMAX media. (Year: 2015).*
Lau, Thorsten, Sylvia Adam, and Patrick Schloss. "Rapid and efficient differentiation of dopaminergic neurons from mouse embryonic stem cells." Neuroreport 17.10 (2006): 975-979. (Year: 2006).*
G.T.-J. Huang, et al., Mesenchymal Stem Cells Derived from Dental Tissues vs. Those from Other Sources: Their Biology and Role in Regenerative Medicine, J Dent Res, 2009, pp. 792-806, vol. 88, No. 9.
Kunimichi Niibe, et al., The potential of enriched mesenchymal stem cells with neural crest cell phenotypes as a cell source for regenerative dentistry, Japanese Dental Science Review, 2017, pp. 25-33, vol. 53.
Steven A. Goldman, Stem and progenitor cell-based therapy of the central nervous system: Hopes, hype and wishful thinking, Cell Stem Cell, 2016, pp. 174-188, vol. 18, No. 2.
Jing Qu, et al., Roles of Mesenchymal Stem Cells in Spinal Cord Injury, Stem Cells International, 2017, pp. 1-12, vol. 2017, Article ID 5251313.
Robert Passier, et al., Origin and use of embryonic and adult stem cells in differentiation and tissue repair, Cardiovascular Research, 2003, pp. 324-335, vol. 58.
Mirella Dottori, et al., Stem Cells as In Vitro Models of Disease, Stem Cells International, 2012, pp. 1-2, vol. 2012, Article ID 565083.
Boon Chin Heng, et al., Small molecules enhance neurogenic differentiation of dental-derived adult stem cells, Archives of Oral Biology, 2019, pp. 26-38, vol. 102.
Jieun Jung, et al., Characterization of Neurogenic Potential of Dental Pulp Stem Cells Cultured in Xeno/Serum-Free Condition: In Vitro and In Vivo Assessment, Stem Cells International, 2016, pp. 1-12, vol. 2016, Article ID 6921097.

* cited by examiner

*Primary Examiner* — Tracy Vivlemore
*Assistant Examiner* — Fatimah Khalaf Matalkah
(74) *Attorney, Agent, or Firm* — Bayramoglu Law Offices LLC

(57) ABSTRACT

A medium-based method for inducing specific differentiation of dental stem cells into dopaminergic neurons is provided. The method includes seeding the dental stem cells at a concentration of 5000 cells/cm$^2$, following 24-hour incubation, introducing the cells into first part neurogenic induction medium and continuing the medium application for 4 days; subsequently, introducing the cells into the second part neurogenic induction medium and continuing the medium application for 2 days; and terminating the differentiation at the end of 6 days. The objective of the present invention is to develop cellular applications for use in treatment of neurodegenerative diseases and medications related to the said diseases.

1 Claim, 15 Drawing Sheets

Day 0

Day 2

Day 4

Day 6

G0/G1 Phase

G2/M Phase

MEDIUM-BASED METHOD REALIZED FOR DIFFERENTIATION OF DENTAL STEM CELLS INTO NEURONS

CROSS REFERENCE TO THE RELATED APPLICATIONS

This application is the national phase entry of International Application No. PCT/TR2021/050426, filed on May 4, 2021, which is based upon and claims priority to Turkish Patent Application No. 2020/06919, filed on May 4, 2020, the entire contents of which are incorporated herein by reference.

TECHNICAL FIELD

The present invention relates to use of a medium-based method for inducing specific differentiation of dental stem cells into dopaminergic neurons.

BACKGROUND

One of the sources of mesenchymal stem cells in the human body is dental tissue. Stem cells isolated from different parts of the tooth are characterized. Examples of these are cells isolated from dental pulp, periodontal connective tissue, and immature impacted teeth [1]. Dental derived stem cells (DDSCs) are remarkable because they originate from neuroectodermal cells (neural crest cells) formed from the ectoderm of the neural tube during the embryonic period [2]. These cells have the capacity to differentiate into many diverse types of cells and tissues. These cells have also been found to possess capacity for osteogenesis, adipogenesis, chondrogenesis, and neurogenesis apart from odontogenesis [1]. Since they originate from neural crest cells and exhibit some neuron-specific expression profiles, DDSCs are seen as promising cell types for treatment of neurodegenerative diseases. The incidence of neurodegenerative diseases, which occur as a result of the increasing and irreversible loss of function or death of nerve cells, is increasing day by day. Reasons such as limited formation of new neurons in the central nervous system, presence of factors that delay recovery, and the skull structure making surgical interventions difficult make the treatment of these types of diseases difficult.

One of the prominent methods for treatment of these diseases caused by nerve cell damage or loss is stem cell applications [3]. It has been observed that after being applied to the determined location with the appropriate technique, stem cells can migrate to the damaged area, have a differentiation capacity, and contribute to the damage repair process by stimulating endogenous stem cells [4]. Today, tissues such as those of teeth, bone marrow, blood, cartilage, and adipose can be used as a source of adult stem cells [5]. Ability of these stem cell types to differentiate into cell types that are lost in neurodegenerative diseases will make it possible to create individual-specific disease models in the laboratory environment with cells prepared from tissues that can be taken from patients more easily from central nervous system tissue [6]. Studying the neurogenic differentiation capacities of these different types of stem cells will enable to determine the cell type and method that can make the greatest contribution for both the replacement of the dead nerve cells in the treatment of neurodegenerative diseases and for the development of various therapies by creating individual-specific cell culture models of these diseases.

Differentiation of induced pluripotent stem cells into neurons has disadvantages such as low differentiation yield in culture, high mutation rate, being more costly than culturing and differentiation of mesenchymal cells, source cells containing viral genes and consequently having considerably high potential of causing carcinogenesis in in vivo cell transfer. In addition, due to the fact that dental stem cells are closer to nerve tissue with respect to embryological origin, it is known that adipose and bone marrow-derived mesenchymal stem cells used in neurogenic differentiation take a longer period of time to transform into nerve cells and do not have as much potential capacity as the dental stem cells. In obtaining mesenchymal stem cells, there arise disadvantages such as methodological difficulty of obtaining cells particularly from bone marrow and cartilage and inability to obtain high amounts of cells. Finally, in the differentiation of stem cells from various origins, the use of substances such as DMSO, BHA or β-mercaptoethanol in the medium which damage the morphological structure of the cell and cause pseudo-neurogenesis in cells makes it impossible to continue the culture of differentiated cells.

The Chinese patent document no. CN104726406, an application known in the art, discloses a method for inducing dental pulp mesenchymal stem cells to be differentiated into nerve cells. In our patent application, additional chemicals (VPA and IBMX) were added as described in the method section and shown in FIGS. 1A-1G in order to stop the cell cycle when the density of cells is between 40-50 percent during the differentiation of stem cells to neurons. This way, the cells were differentiated in a healthy manner and as induced towards neural lineage not due to the high density but due to the method applied.

The Chinese patent document no. CN1590537, an application known in the art, discloses a method for separating and culturing the ectomesenchyme stem cells. Within the scope of the invention, the method can be used for bone tissue engineering, muscle tissue engineering, tooth tissue engineering and repairing peripheral nerve cells. Furthermore, a differentiation procedure for the glial lineage instead of the neural lineage was used in the said patent application to ensure regeneration of peripheral nerve cells. In addition, it differs from our patent application methodologically since only forskolin chemical is used and it consists of a single step. As known in the literature, it has been shown that use of cyclic-amp activators such as forskolin alone in differentiation is not sufficient. At the same time, the reliability of the differentiation method in our patent application has been proved both morphologically and by using cresyl violet staining (FIGS. 2, 3A, and 3B). For all the reasons explained above, it has been observed that the method in our patent application is more effective.

The United States patent application document numbered US2016296669, one of the state of the art applications, discloses a method for producing graft material for treating nerve damage. The method of the said invention includes a step of culturing dental pulp stem cells in a medium containing no growth factors except FGF2 (or bFGF (Basic Fibroblast Growth Factor)). In addition, it is known that the FGF2 factor used in the said patent document activates only the genes associated with the neural lineage of dental pulp-derived stem cells. However, it is known that many signaling pathways, including the cell cycle, play a key role in the differentiation of stem cells. Therefore, it is clear that the administration of only the FGF2 factor to the stem cells does not provide a valid neural cell transformation. Taking these into consideration, it has been shown that the invention of our patent application has a mature and functional neuron genetic expression as shown in FIGS. 4A-4H as a result of following a protocol consisting of two steps in order to both activate differentiation pathways and mature the neural cells, as also described in the method.

SUMMARY

The objective of the present invention is medium-based differentiation of dental derived stem cells into dopaminergic neurons.

Another objective of the present invention is to develop cellular applications for use in treatment of neurodegenerative diseases and medications related to the said diseases.

BRIEF DESCRIPTION OF THE DRAWINGS

FIGS. 1A-1G show representations of the effect of the neurogenic induction medium created within the scope of the invention on the cell cycle of the cells depending on the days, wherein FIGS. 1A-1D show cell cycle graphics of cells treated with neurogenic induction medium for 0, 2, 4 and 6 days, FIG. 1E shows a graphical representation of cells in G0/G1 Phase in percentage, FIG. 1F shows a graphical representation of cells in S Phase in percentage, and FIG. 1G shows a graphical representation of cells in G2/M Phase in percentage.

FIGS. 3A-3B show light microscopy images of the cells that have been subjected to neurogenic induction medium for 6 days within the scope of the invention and the control cells grown only in the medium after staining with Cresyl Violet stain specific to neurogenic cells, wherein FIG. 3A: Neurogenic Medium, and FIG. 3B: Control.

FIGS. 4A-4H show graphical representations of measurement of the genes specific to neurogenic cells in the cells that have been subjected to neurogenic induction medium for 6 days within the scope of the invention and the control cells grown only in the medium, wherein FIG. 4A: NeuN gene, FIG. 4B: Nurrl gene, FIG. 4C: DAT gene, FIG. 4D: Snap 25 gene, FIG. 4E: NF—H gene, FIG. 4F: Map2 gene, FIG. 4G: TH gene, and FIG. 4H: Bcl-2 gene.

Figures 1A, 1B:
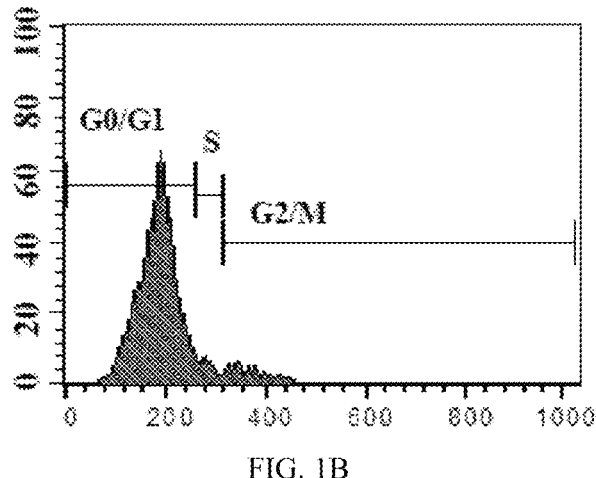
Figures 1C, 1D:
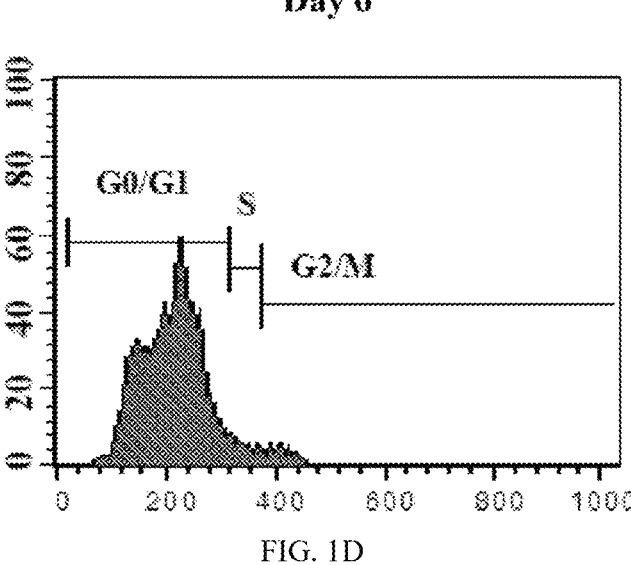
Figure 1E:
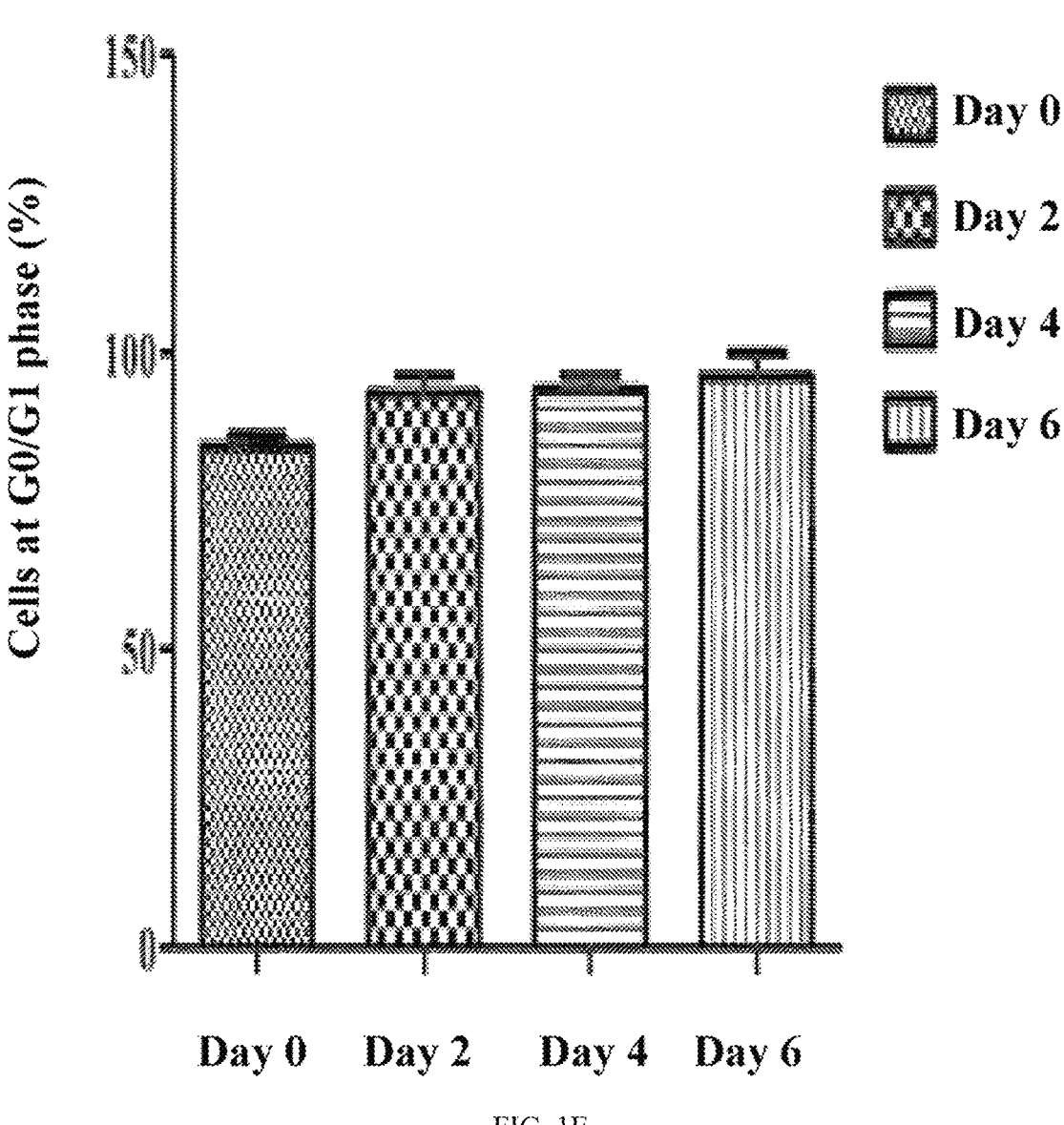
Figure 1F:
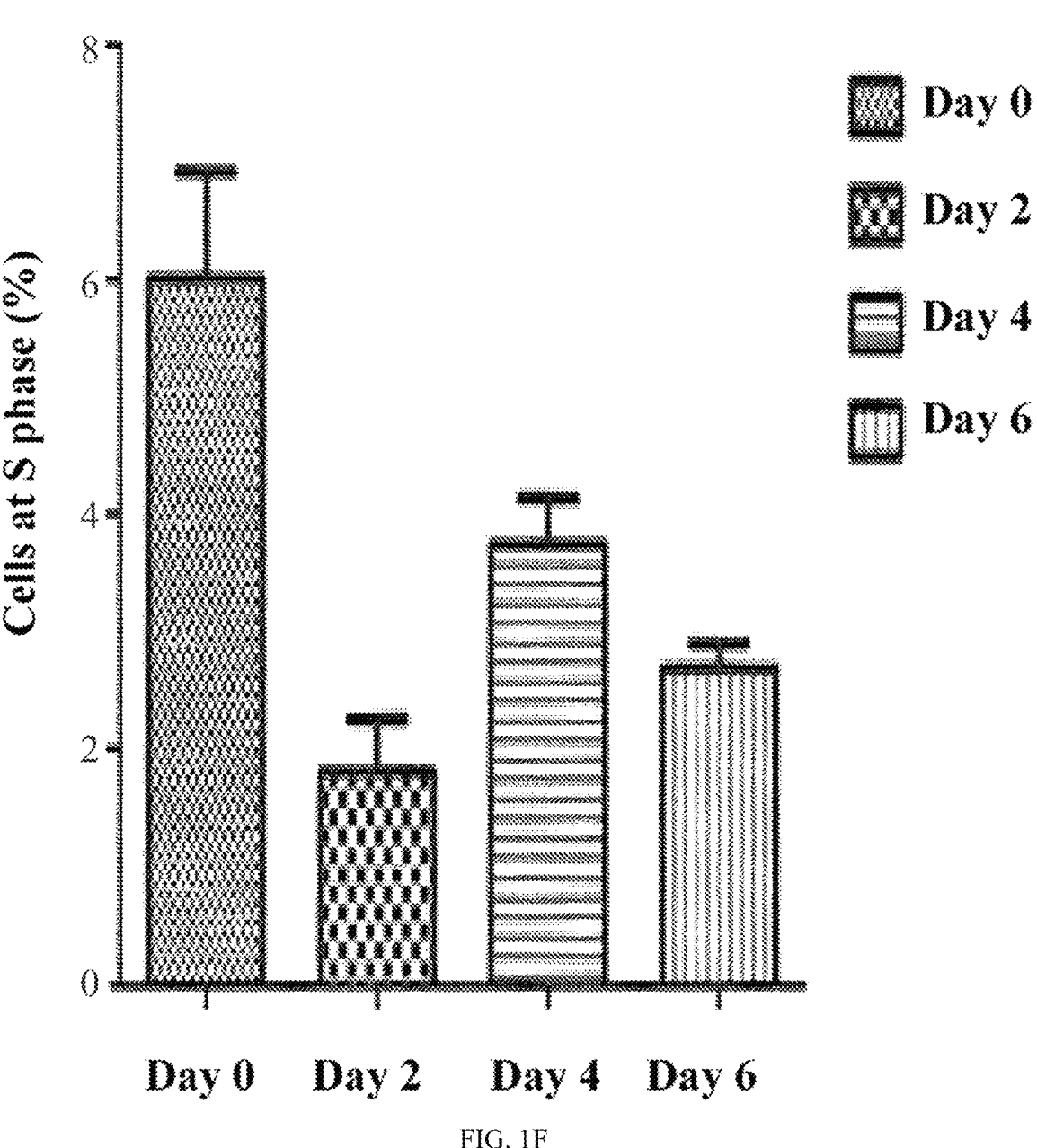
Figure 1G:
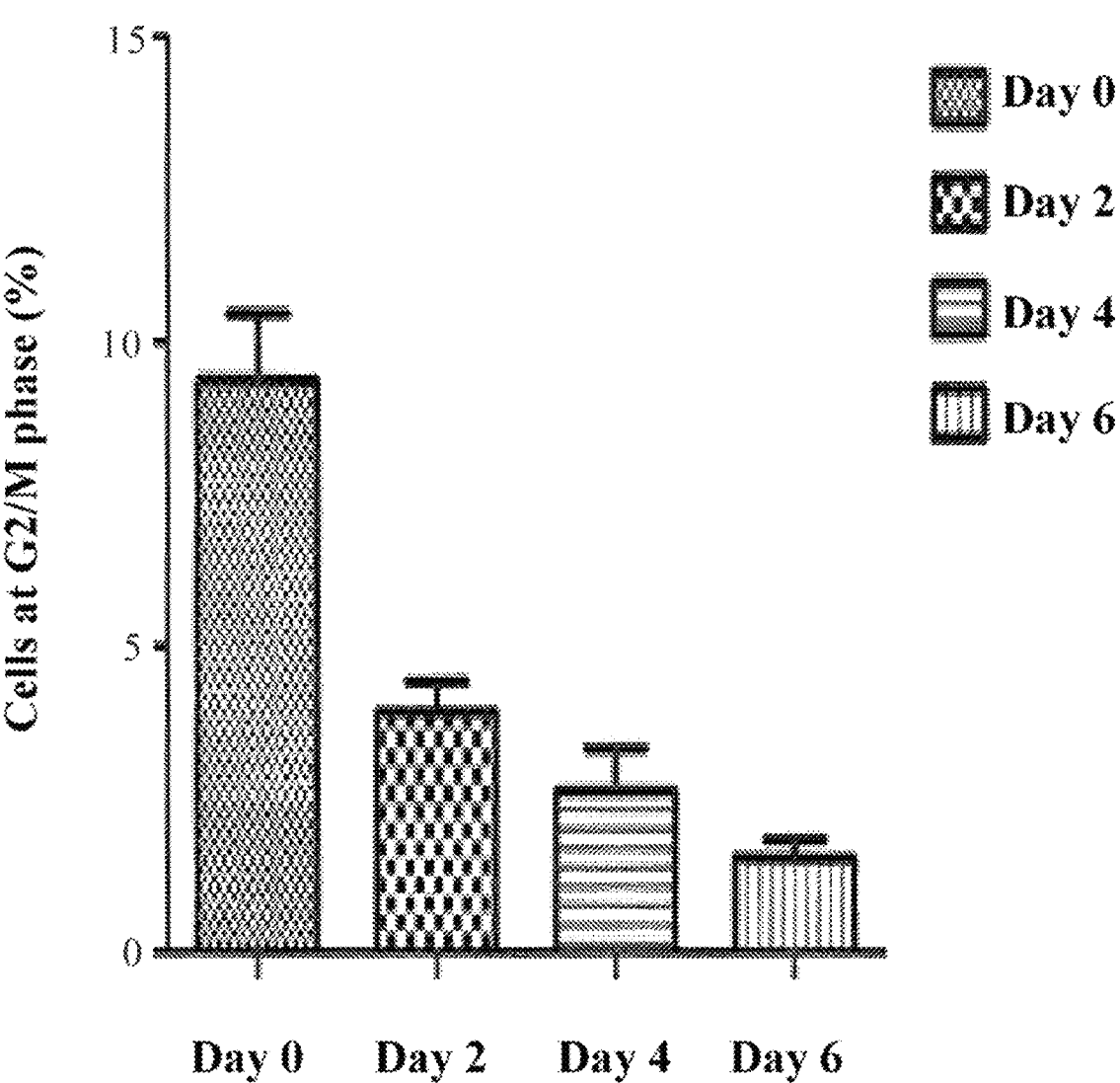
Figure 2:
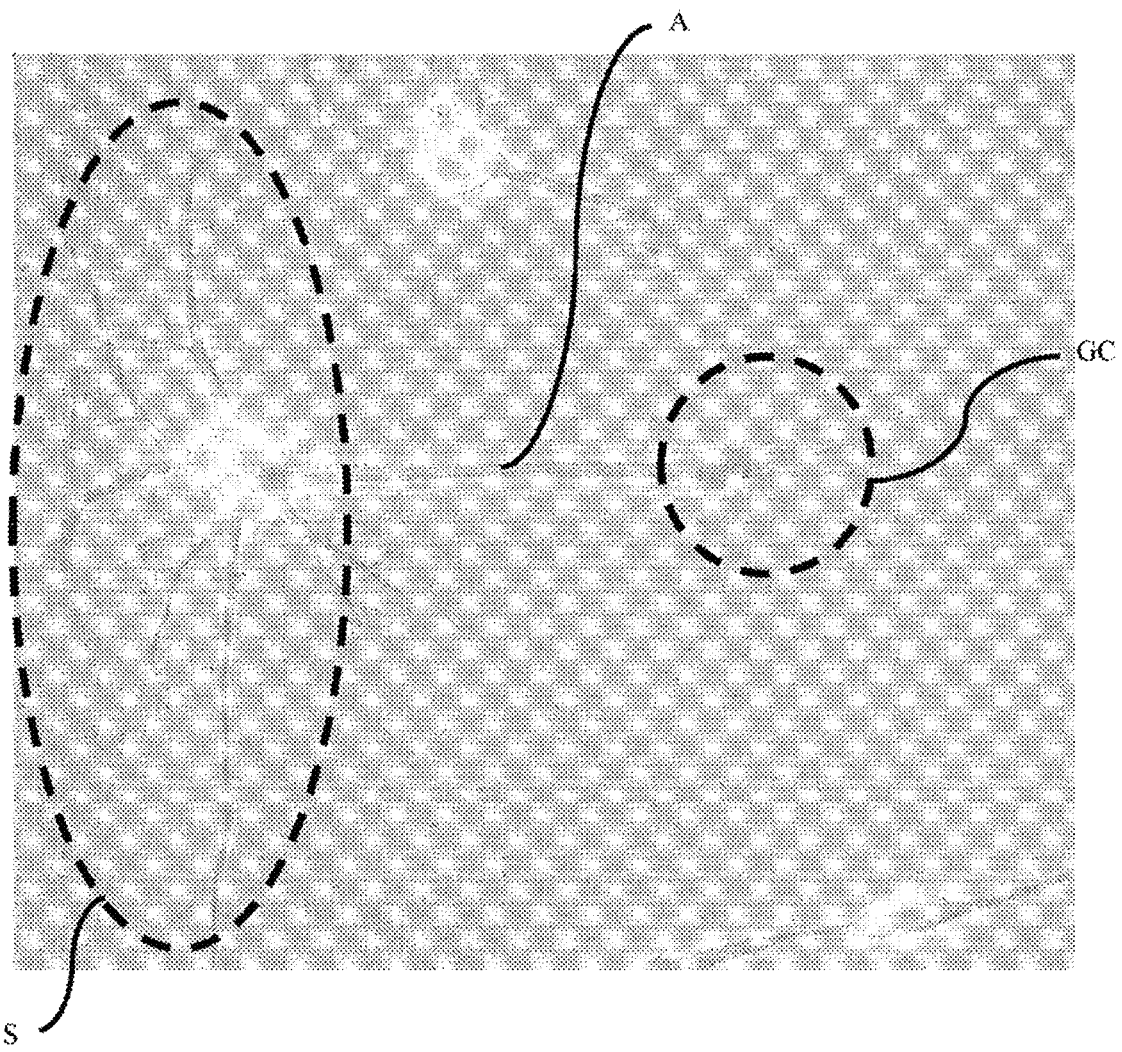
FIG. 2 shows morphological examination of the cells that have been subjected to neurogenic induction medium for 6 days within the scope of the invention; microscopic image of the cell soma specific to neurons, an elongated axon and a growth cone in the said cell. The components shown in FIG. 2 are each given reference numbers as follows: A. Axon; S. Soma; and GC. Growth Cone.
Figure 3A:
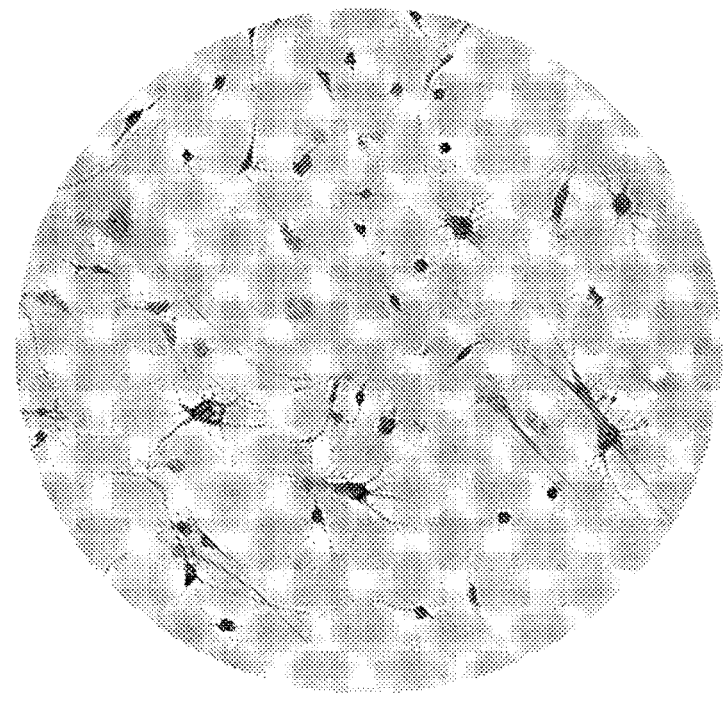
Figure 3B:
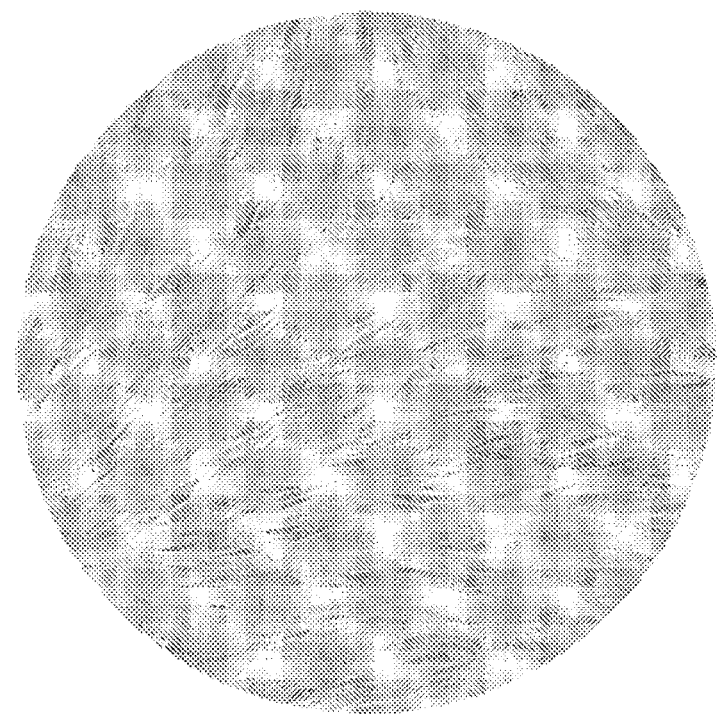
Figure 4A:
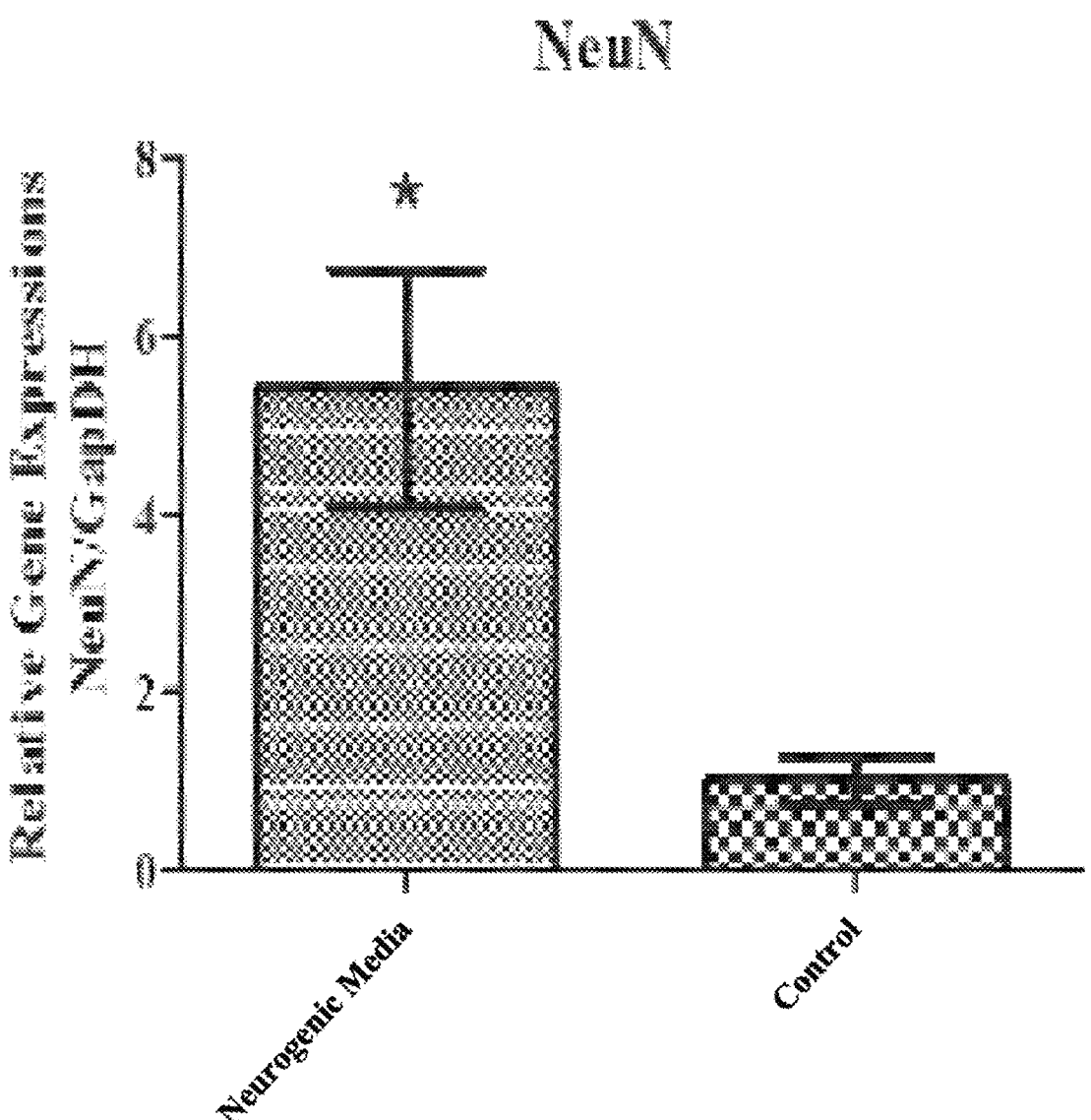
Figure 4B:
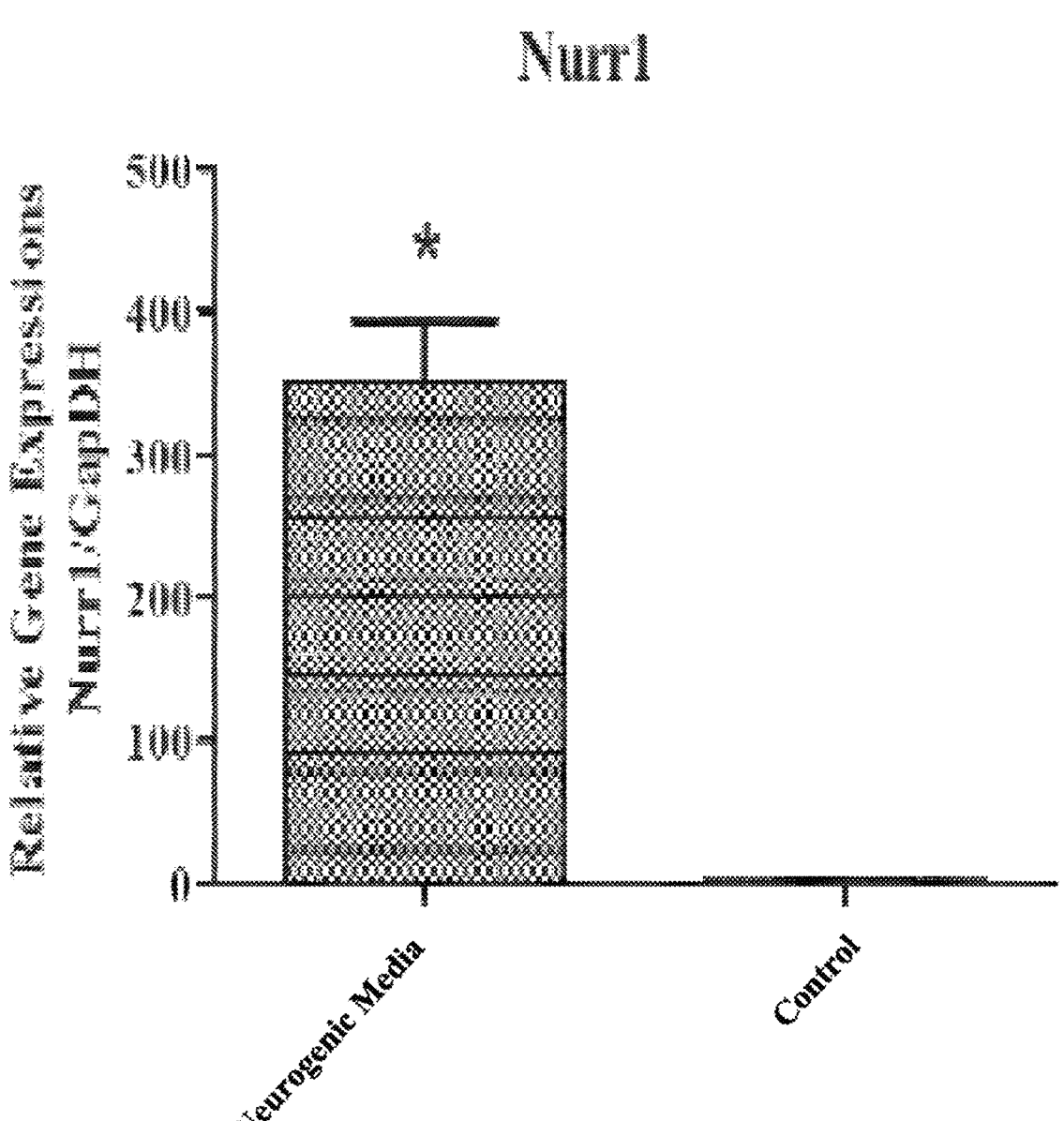
Figure 4C:
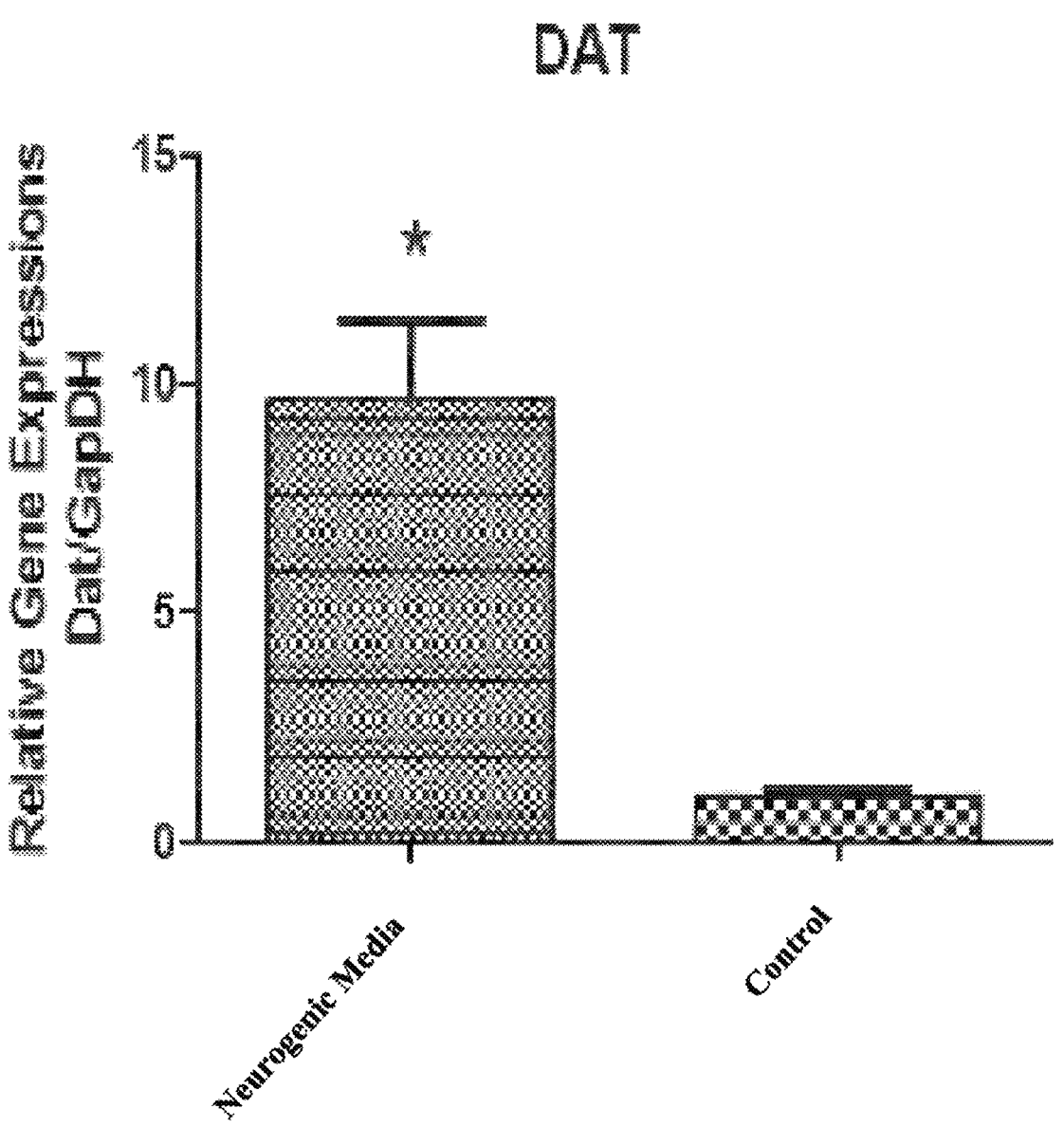
Figure 4D:
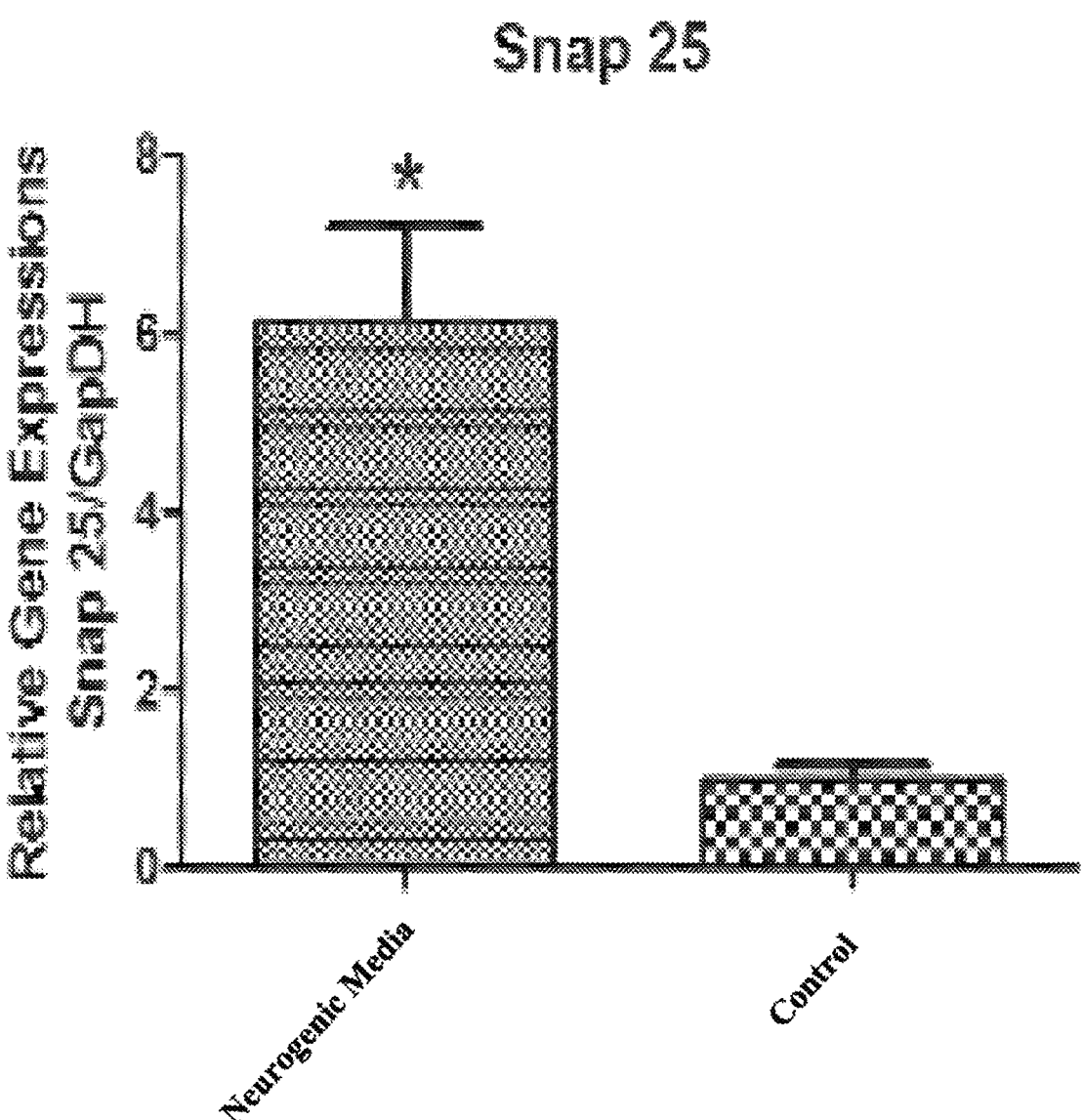
Figure 4E:
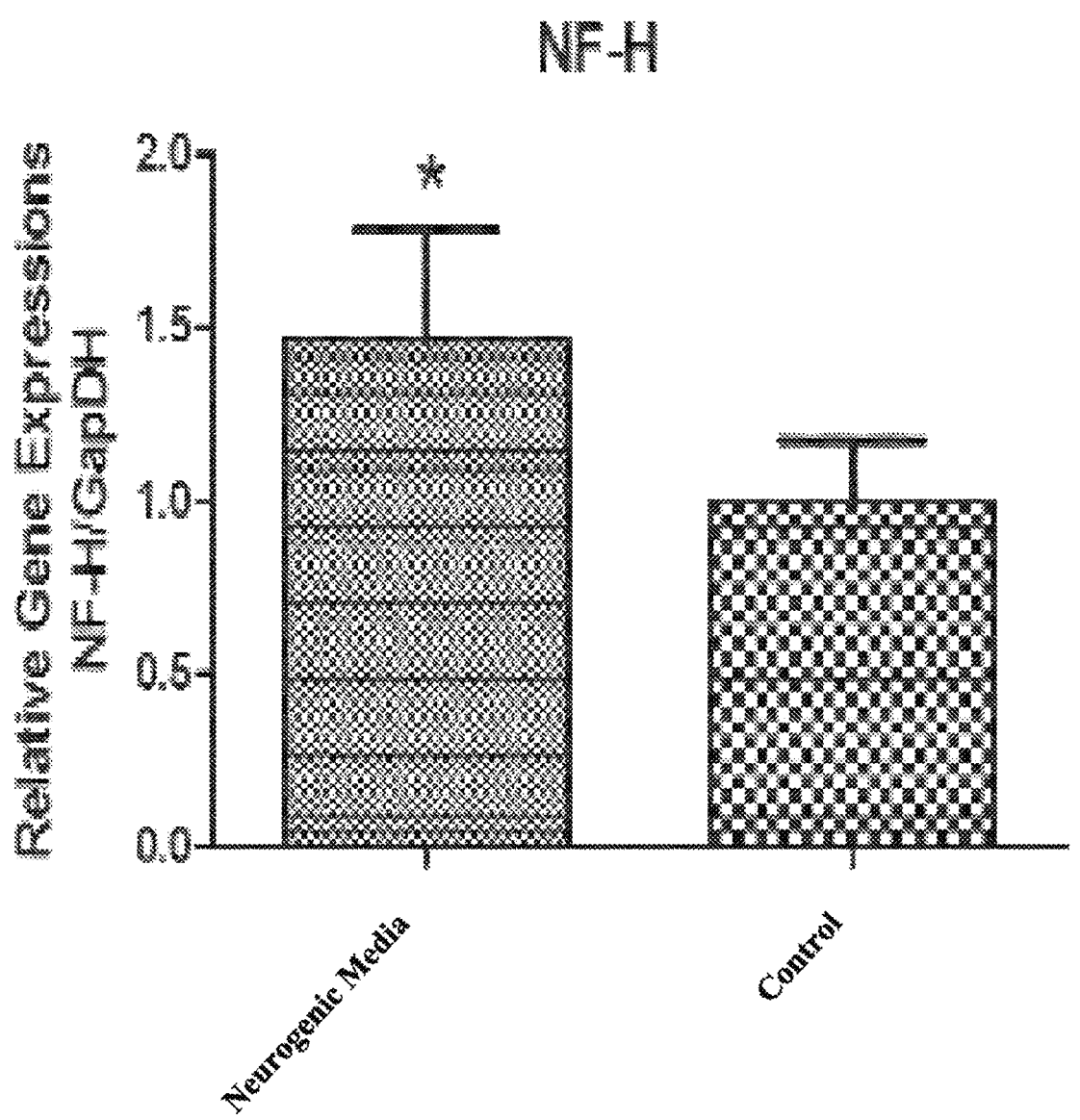
Figure 4F:
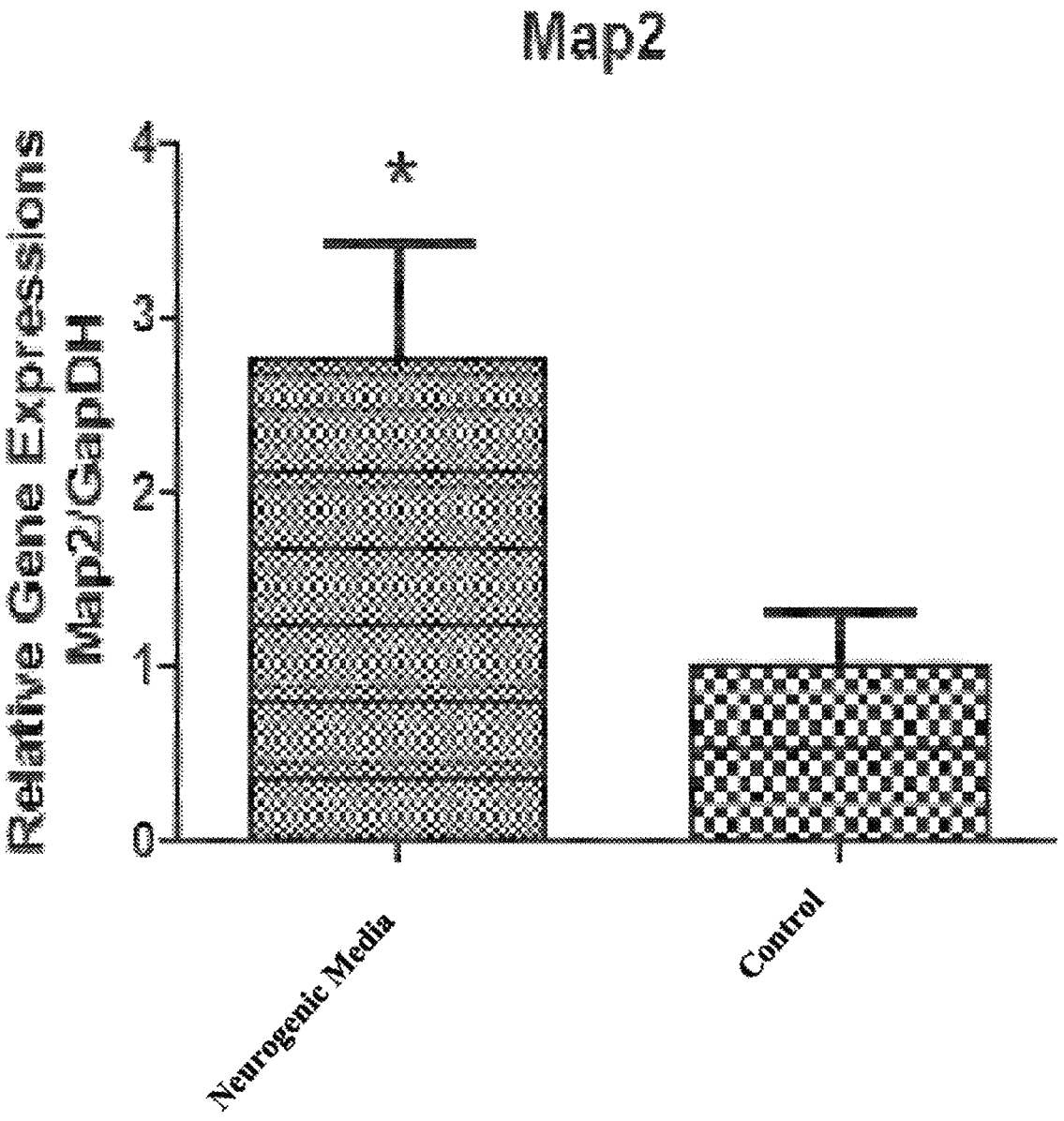
Figure 4G:
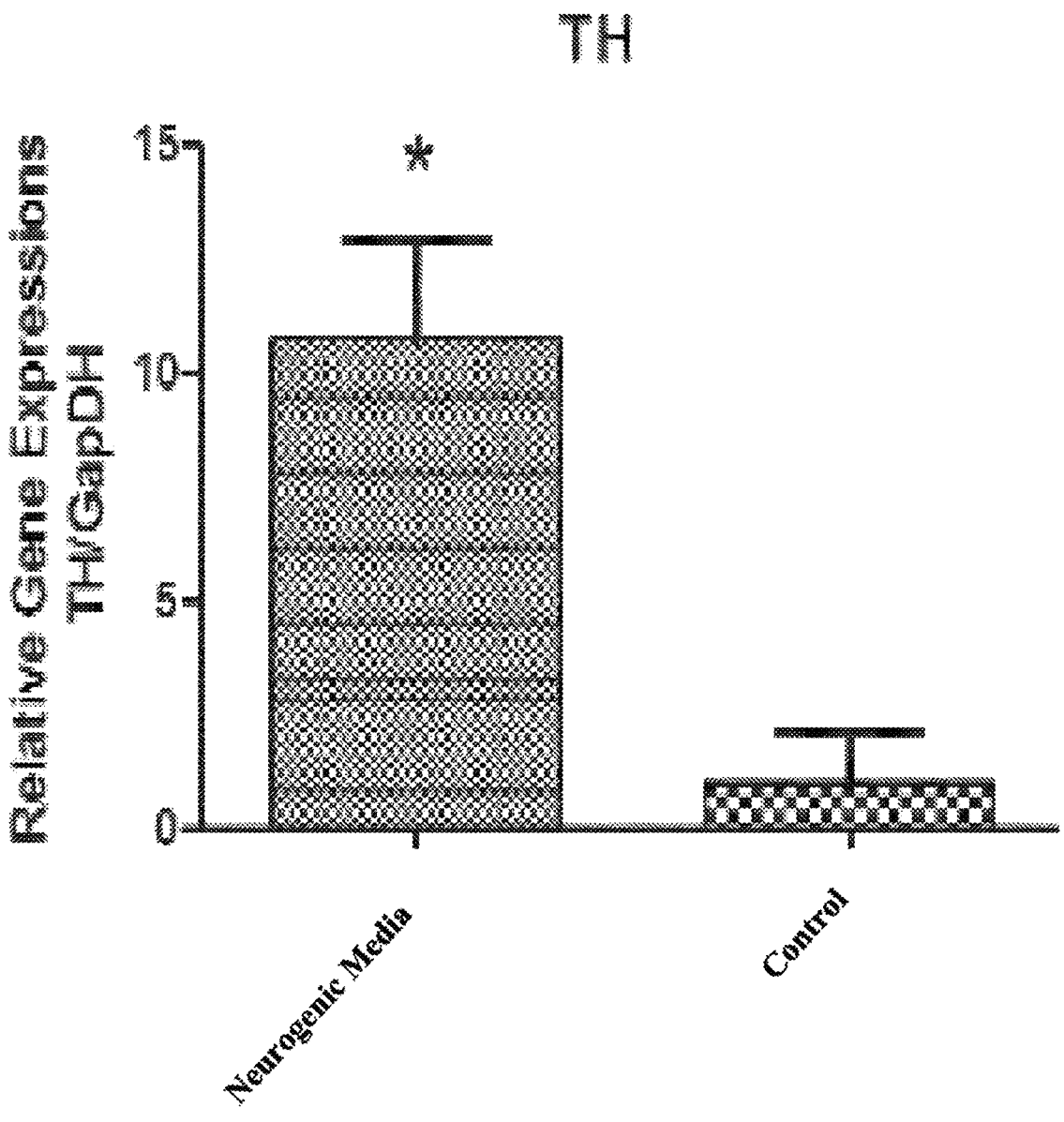
Figure 4H:
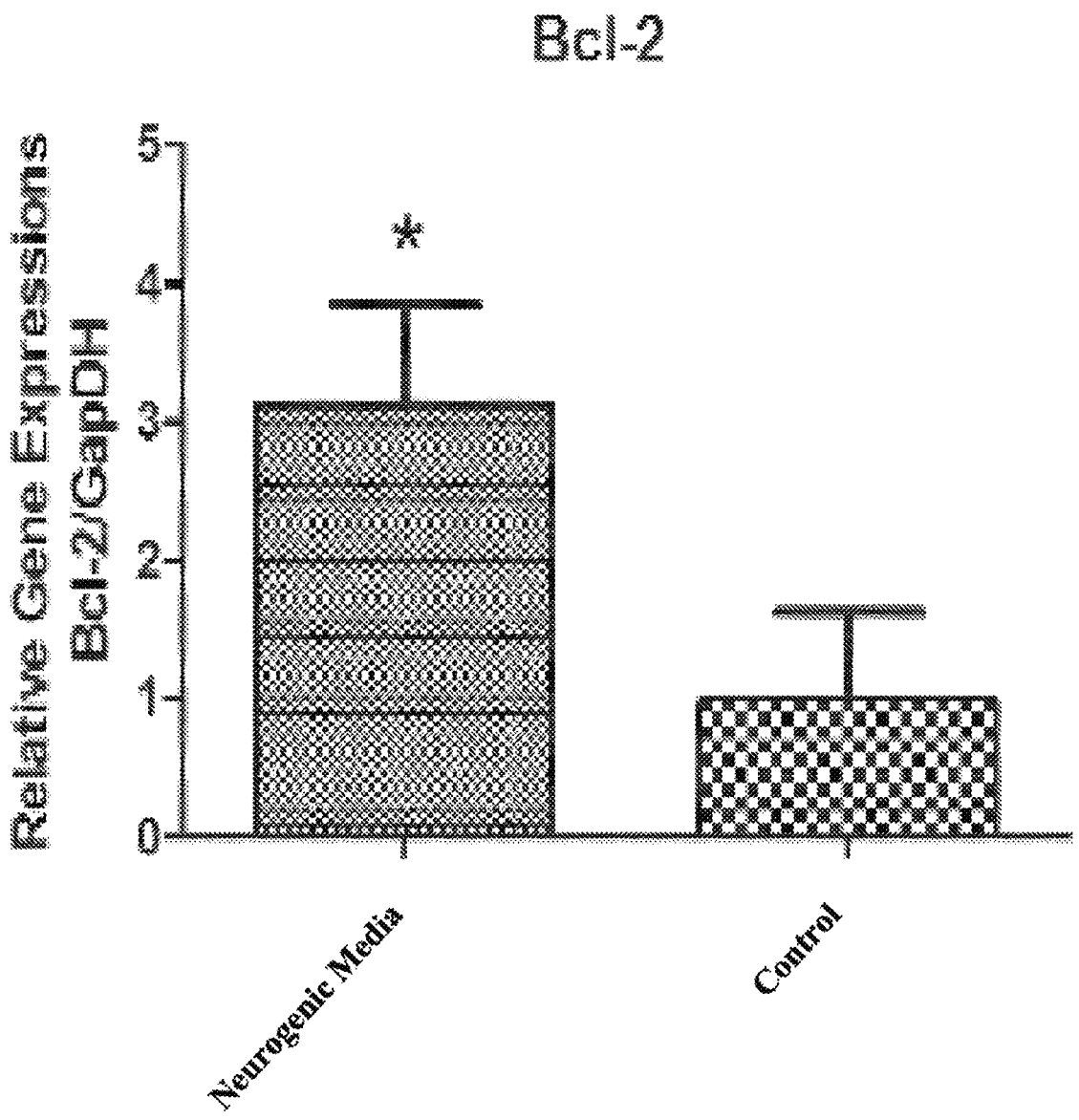

The components shown in the figures are each given reference numbers as follows:

A. Axon
S. Soma
GC. Growth Cone

DETAILED DESCRIPTION OF THE EMBODIMENTS

Within the scope of the invention, a study is conducted in the fields of cellular applications for use in the treatment of neurodegenerative diseases and the development of drugs related to these diseases, cell differentiation studies in the laboratory, drug development for the treatment of cancer types such as neuroblastoma. Accordingly, a novel medium-based application has been developed within the scope of the invention in order to specifically induce differentiation of stem cells obtained from teeth into dopaminergic neurons.

In applications of differentiation from stem cells into neurons, considering the facts that the dental stem cells are closer to the nerve tissue with respect to embryological origin and that the transformation of adipose (cartilage) and bone marrow-derived mesenchymal stem cells, which are used in the state of the art in neurogenic differentiation, into neurons takes a longer period of time, it is seen that dental stem cells have a higher potential capacity for differentiation into neurons compared to the applications known in the art.

The method of neurogenic differentiation of dental stem cells carried out within the scope of the invention comprises the following steps:

Seeding the dental stem cells at a concentration of 5000 cells/cm$^2$

Following 24 hour incubation, introducing the cells into first part neurogenic induction medium and continuing the medium application for 4 days, Subsequently, introducing the cells into the second part neurogenic induction medium and continuing the medium application for 2 days, Terminating the differentiation at the end of 6 days.

The contents of the first part and second part neurogenic induction media expressed in the above method are as follows:

Neurogenic Induction Medium Part 1:
Dmem/F12 Glutamax supplement
B-27 Supplement 1%
3-Isobutyl-1-methylxanthine (IBMX) 100 μM
Valproic acid sodium salt (VPA) 2 mM
Forskolin 0.1 μM
Basic Fibroblast Growth Factor (bFGF) 20 ng/ml
Epidermal Growth Factor (EGF) 20 ng/ml Neurogenic Induction Medium Part 2:
Dmem/F12 Glutamax supplement
B-27 Supplement 1%
3-Isobutyl-1-methylxanthine (IBMX) 100 μM
Valproic acid sodium salt (VPA) 2 mM
Forskolin 0.1 μM
Basic Fibroblast Growth Factor (bFGF) 20 ng/ml
Epidermal Growth Factor (EGF) 20 ng/ml
Brain derived neurotrophic factor 30 ng/ml Advantages provided by means of the present invention can be listed as follows:

Provides effective neuronal differentiation in mesenchymal stem cells instead of induced pluripotent stem cell.

Neuronal differentiation is observed in a shorter period of time compared to other differentiation media and protocols.

A more efficient neuron formation is observed compared to other differentiation media and protocols.

While neuronal differentiation of cells differentiated by other media is reversible, cells differentiated within the scope of the present invention exhibit terminal transformation.

As shown in the figures as well, the cell cycle stops as of day 2, which is necessary for an effective differentiation.

Does not cause any toxicity on the cells when compared with the other media.

While these neuronal cells can be used in tissue regeneration and transplantation, they also provide a great contribution to neuroscience studies.

Experimental Studies

Cell Cycle Assay

Flow cytometry analyses of dental stem cells treated with neurogenic media are performed in order to observe the changes of their phases in the cell cycle. For the cell cycle assay, the cells fixed on the second, fourth and sixth days in the neurogenic differentiation process were analyzed by treating with RNase A and Nonidet P40 and staining with propidium iodide.

Real Time Polymerase Chain Reaction

Real-time polymerase chain reaction assay is performed to observe the changes in the gene levels of the cells treated with neurogenic medium. These changes are both at morphological level and gene expression level. The primers that were used were designed using Primer BLAST software (The National Center for Biotechnology=NCBI). Total RNAs were isolated from the cells on which gel combination was applied and cDNA was synthesized. The synthesized cDNAs were mixed with primers in Fermentas Maxima SYBR Green mixture product such that the final volume will be 20 µl and the expression levels of the genes were analyzed by using BIO-RAD device.

Morphological Analysis of Differentiated Cells

On the last day of differentiation process of the cells treated with neurogenic medium, morphological analyses of the cells were performed under light microscope. While analyzing the differentiated cells, the development and existence of characteristic cells and structures in neurons were morphologically examined.

Cresyl Violet Staining of Differentiated Cells

On the last day of differentiation process of the cells treated with neurogenic medium, staining of the characteristic nissl bodies seen in cells which are specific to neurons was performed. The cresyl violet stain which is applied to the cells stains the ribosomes of the granular endoplasmic reticules found in the soma (S) of the nerve cells and reveals a dark blue-purple color. Undifferentiated dental stem cells on the other hand can be detected in pale pink.

REFERENCES

[1]. Huang, G. T., S. Gronthos, and S. Shi, *Mesenchymal stem cells derived from dental tissues vs. those from other sources: their biology and role in regenerative medicine.* J Dent Res, 2009. 88(9): p. 792-806.

[2]. Niibe, K., et al., *The potential of enriched mesenchymal stem cells with neural crest cell phenotypes as a cell source for regenerative dentistry.* Jpn Dent Sci Rev, 2017. 53(2): p. 25-33.

[3]. Goldman, S. A., *Stem and Progenitor Cell-Based Therapy of the Central Nervous System: Hopes, Hype, and Wishful Thinking.* Cell Stem Cell, 2016. 18(2): p. 174-88.

[4]. Qu, J. and H. Zhang, *Roles of Mesenchymal Stem Cells in Spinal Cord Injury.* Stem Cells Int, 2017. 2017: p. 5251313.

[5]. Passier, R. and C. Mummery, *Origin and use of embryonic and adult stem cells in differentiation and tissue repair.* Cardiovasc Res, 2003. 58(2): p. 324-35.

[6]. Ruiz-Lozano, P. and P. Rajan, *Stem cells as in vitro models of disease.* Curr Stem Cell Res Ther, 2007. 2(4): p. 280-92.

What is claimed is:

1. A medium-based method realized for a differentiation of dental stem cells into neurons, wherein the medium-based method enables mesenchymal stem cells obtained from a dental tissue to be differentiated into dopaminergic neurons, and the medium-based method comprises:

seeding the dental stem cells at a concentration of 5000 cells/cm$^2$, following a 24-hour incubation, introducing the dental stem cells into a first part neurogenic induction medium and continuing a first medium application for 4 days, subsequently, introducing the dental stem cells into a second part neurogenic induction medium and continuing a second medium application for 2 days, and terminating the differentiation at an end of 6 days, wherein the first part neurogenic induction medium comprises:

Dulbecco's Modified Eagle Medium/Ham's F-12 (DMEM/F12) medium supplemented with L-alanyl-L-glutamine, a serum-free neuronal supplement at 1%, 3-isobutyl-1-methylxanthine (IBMX) 100 µM, a valproic acid sodium salt (VPA) 2 mM, forskolin 0.1 µM, basic fibroblast growth factor (bFGF) 20 ng/ml, and epidermal growth factor (EGF) 20 ng/ml; and the second part neurogenic induction medium comprises:

DMEM/F12 medium supplemented with L-alanyl-L-glutamine, a serum-free neuronal supplement at 1%,

IBMX 100 µM,

VPA 2 mM, forskolin 0.1 µM, bFGF 20 ng/ml,

EGF 20 ng/ml, and a brain-derived neurotrophic factor 30 ng/ml.

* * * * *